United States Patent [19]
Newkome et al.

[11] Patent Number: 5,886,126
[45] Date of Patent: Mar. 23, 1999

[54] COMBINATORIAL METHOD OF FORMING CASCADE POLYMER SURFACES

[75] Inventors: George R. Newkome, Temple Terrace; Charles N. Moorefield, Tampa, both of Fla.

[73] Assignee: University of South Florida, Tampa, Fla.

[21] Appl. No.: 705,905

[22] Filed: Aug. 28, 1996

[51] Int. Cl.$^6$ .................................................. C08G 18/71
[52] U.S. Cl. ........................... 528/49; 525/440; 525/452; 525/474
[58] Field of Search .................... 525/440, 452, 525/474; 528/49

[56] References Cited

U.S. PATENT DOCUMENTS

| | | | |
|---|---|---|---|
| 5,414,075 | 5/1995 | Swan et al. | 568/333 |
| 5,610,268 | 3/1997 | Meijer et al. | 528/363 |

OTHER PUBLICATIONS

Wörner, C. et al., *Anges Che., Int. Ed. Engl.* (1993), 32:1306; *Agnew Chem.* (1993), 105:1367; deBrabander–van den Berg et al. *Agnew Chem., Int.Ec. Engl.* (1993) 32:1308, *Agnew., Chem.* (1993) 105:1370.

Xiang, et al. *Science* (1995) 268:1738.

Plattner et al., *J. Am. Chem. Soc.* (1972) 94:8613.

van Gendersen et al., *Recl. Trav. Chim. Pays–Bas.* (1994) 113:573; Domingeuz et al., *J. Org. Chem.* (1961) 26:1625.

Carell et al., *Chem. & Biol.* (1995) 2:171; Carell et al., *Agnew Chem. Int. Ed. Eng.* (1994) 33:2059.

*Primary Examiner*—Rachel Gorr
*Attorney, Agent, or Firm*—Kohn & Associates

[57] ABSTRACT

The method of forming a surface layer on a substrate is accomplished by dendrimerizing a mixture of branched monomers on the substrate surface wherein the monomers have heterogeneous functionalized branches and homogenous connectivity to the substrate. A cascade polymer coated substrate is formed consisting essentially of a substrate including a surface and at least one dendrimerized surface layer consisting of heterogeneous functionalities the layer being linked to the substrate by homogenous linkages, preferably isocyanate linkages.

10 Claims, 3 Drawing Sheets

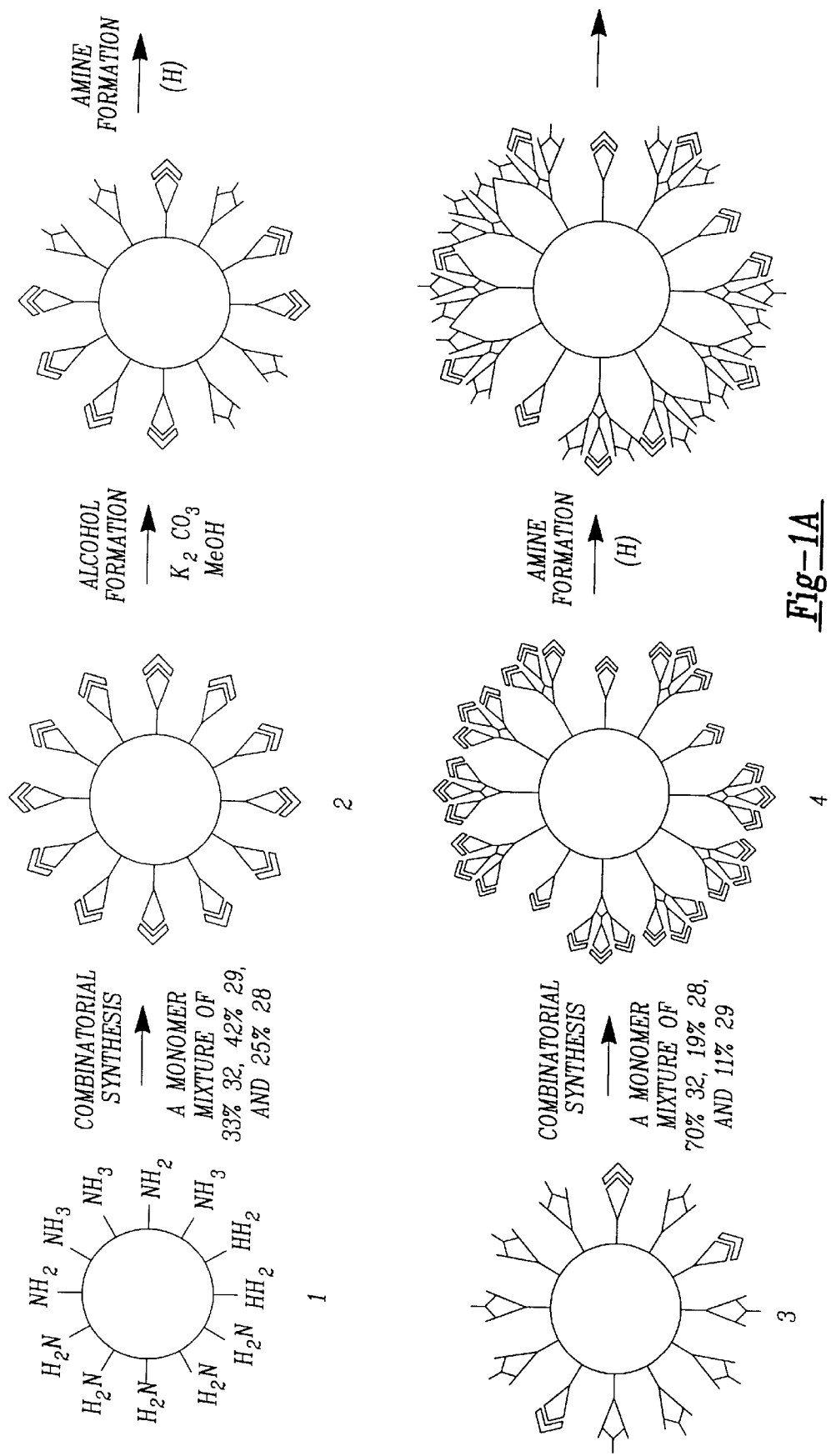

COMBINATORIAL METHOD OF FORMING CASCADE POLYMER SURFACES

GRANT REFERENCE

The research carried out in connection with this invention was supported in part by a grant from the National Science Foundation, grant number DMR-92-17331.

TECHNICAL FIELD

The present invention relates to highly branched molecules possessing a three dimensional morphology. More specifically, the present invention relates to cascade polymers as molecules per se or as surfaces applied to various substrates. Such molecules and substrates possess uses in areas such as detergents, radio imaging, binding sites for drug delivery, polyfunctional basis and other areas of use.

BACKGROUND OF THE INVENTION

The U.S. patent application Ser. No. 08/626,395, filed Apr. 2, 1996, discloses a method of synthesizing multi-tier cascade polymers, as well as coating substrate surfaces, utilizing a novel family of stable trifunctionalized isocyanates. Continuing with applicants' previous work utilizing dendrimeric monomer building blocks to construct cascade polymers of predetermined internal and external architecture, applicants have begun to realize and further materialize some of the potential uses of the novel isocyanate building blocks. Previous work by applicants in forming cascade polymers were limited to the coupling of an acid (dendritic termi) and an amine. In an effort to bypass this relatively limited combination, applicants demonstrated the facile conversion of unique, sterically protected, "Behera's Amine" to the corresponding isocyanate by its treatment with triphogene (commercially available from Aldrich Chemical Co., catalog #33,075-2, referred to as "bis (trichloromethyl)carbonate") in the presence of triethylamine[1,2].

The isocyanate monomers are excellent building blocks or modules for use in the transformation and introduction of surface functionality or either a cascade polymer under construction or on surfaces of substrates in general. The isocyanate based monomers also provide for rapid, iterative tier construction. That is, the layering of tiers or layers over a surface or about an existing cascade polymer can be performed relatively rapidly using the isocyanate monomers. Preliminary evaluations by applicants have demonstrated the facile reaction of Behera's isocyanate with generations 2 through 5 (8, 16, 32, 64 termini, respectively) of amine terminated, poly(propylene imine) dendrimers [3] using tert-butyl alcohol as solvent. In this case, the reaction of Behera's amine isocyanate building block with the poly (propylene imine) dendrimers constitutes the formation of a new dendrimer, using the dendrimers prepared as described by Worner and Mulhaupt[3], as the starting core. This confirms the potential of the monomer to react with nucleophilic groups, as well as affords a reasonable insight into the reactivity potential for other hindered isocyanate building blocks. Stoichiometric reactions result in the isolation of pure (95% or greater) surface modified dendrimer with no by-products. These materials can be sequentially deprotected and subjected to further elaboration.

In view of the above, there is significant demonstration that the isocyanate based building blocks can be employed to "dendrimerize" any common material(s) possessing an acidic proton(s). Examples of such substrates include silica based substances, functionalized classical linear polymers, functionalized classical micelles, microgels and spherical polymers and as demonstrated via reaction with the poly (propylene imine) dendrimers, cascade polymers. Such surface coatings or films are useful for the creation of thermally and chemically stable coatings. Thus, these coatings can be used as protective coatings on clothing, other fabrics, metal surfaces, composite-based materials, or the like. Surface property modification, such as wetability, is also possible.

Biological molecules are often identified by the synthesis and screening of large collections (termed "libraries") of structures. Such methods are commonly employed with the humoral immune system, which can generate and screen some $10^{12}$ antibody molecules to identify one that specifically recognizes and binds a foreign pathogen. The development of catalytic antibodies was one of the first applications of such molecular libraries to chemistry. Other such methods have been further developed for generating and screening large populations of biological molecules in vitro for binding, catalysts or both. A large effort has been devoted towards the application of these "combinatorial libraries". Such libraries are generated by combining large numbers of precursors.

The present invention relates to the further advancement of the use of monomers normally employed in the preparation of cascade polymers and more specifically to stable multifunctionalized isocyanates in combination with combinatorial chemistry to provide novel surface layers on substrates. That is, the potential to create and utilize new materials prepared "combinatorially" is exploited by the present invention. An advancement in cascade polymer dendrimeric chemistry is derived wherein combinatorial [4] methods of dendritic construction utilize mixtures possessing varying compositions of differing monomers (preferably isocyanate based monomers) for sequential tier formation.

SUMMARY OF THE INVENTION

In accordance with the present invention, there is provided a method of forming a surface layer on a substrate by dendrimerizing a mixture of branched monomers on the substrate wherein the monomers have heterogenously functionalized branches and homogenous connectivity to the substrate.

The present invention further provides a cascade polymer coated molecule consisting essentially of a substrate including a surface and at least one dendrimerized surface layer consisting of heterogeneous functionalities, the layer being linked to the substrate by homogenous linkages.

DETAILED DESCRIPTION OF THE DRAWINGS

Figure 1B:
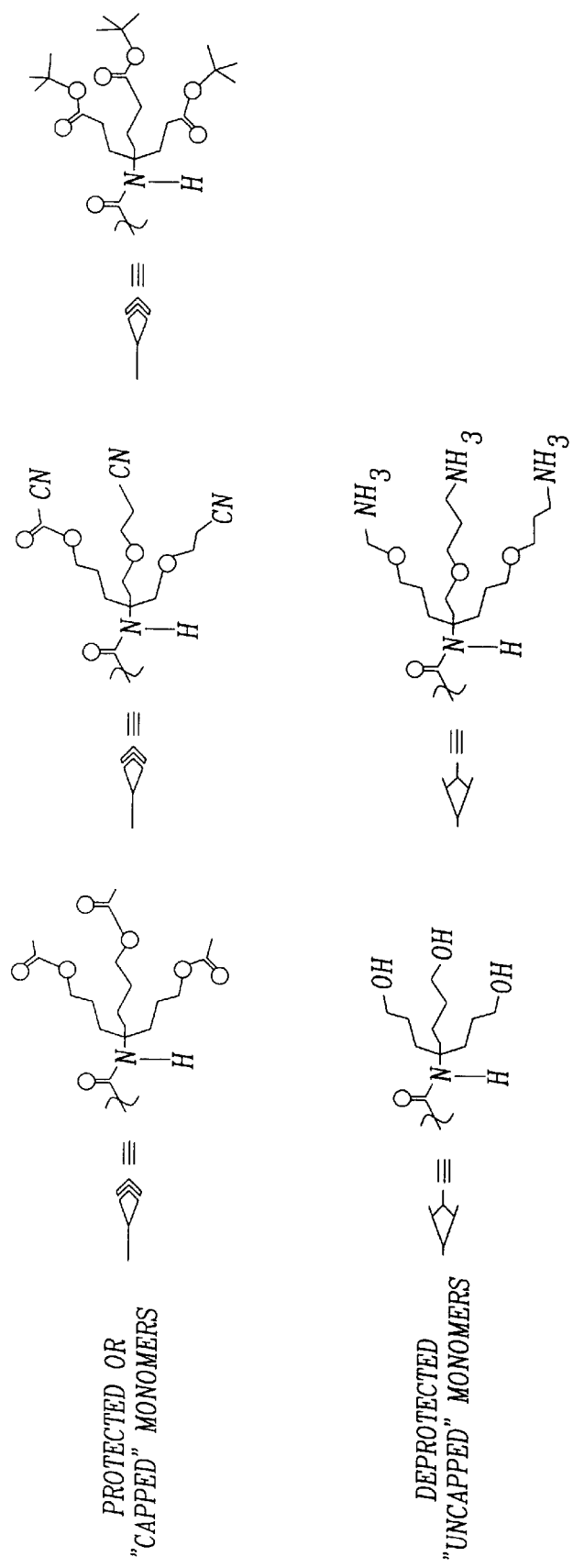
Figure 2:
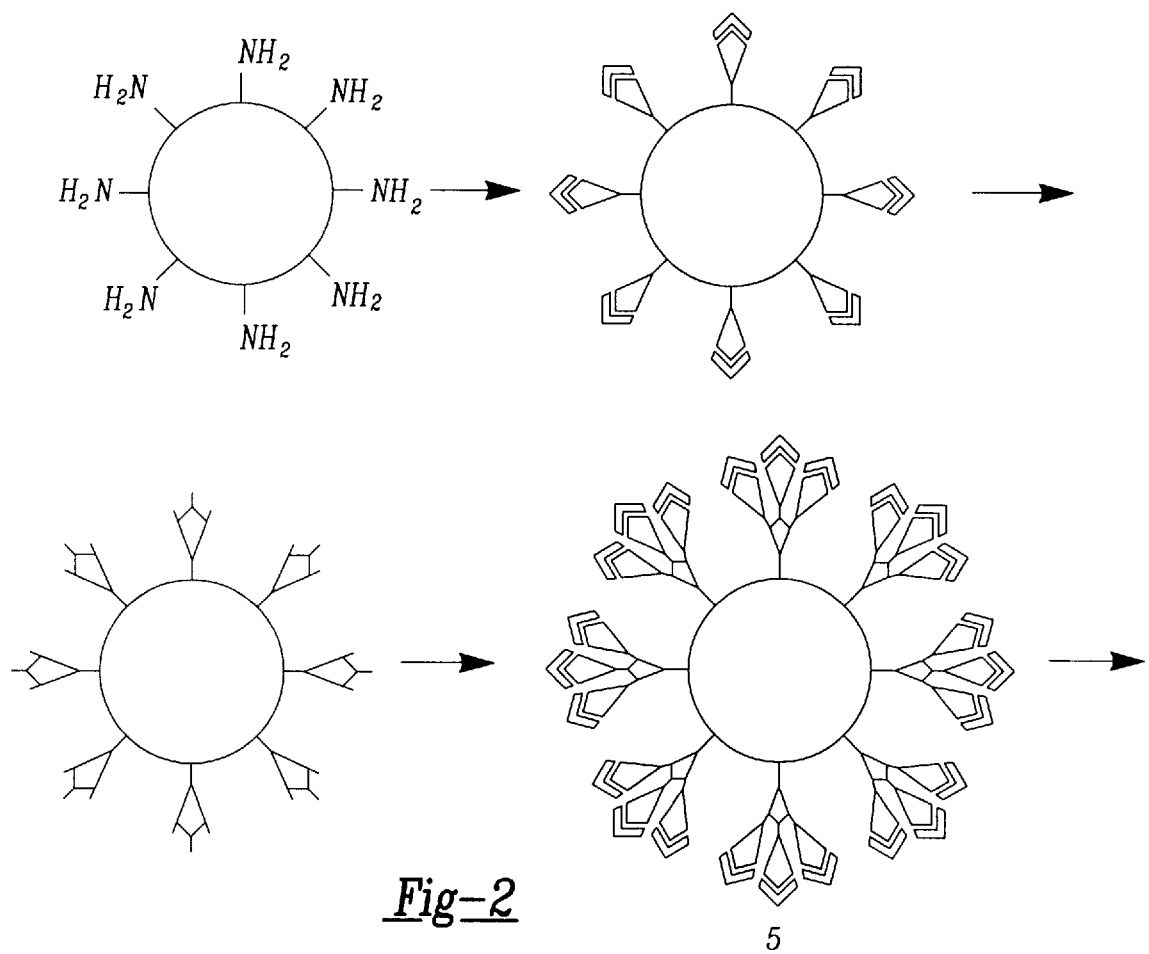

Other advantages of the present invention will be readily appreciated as the same becomes better understood by reference to the following detailed description when considered in connection with the accompanying drawings wherein:

FIG. 1 is a schematic representation of combinatorial based dendritic construction of dendrimers made in accordance with the present invention; and FIG. 2 is a schematic representation of hydrolytic, combinatorial based, dendritic materials made in accordance with the present invention.

DETAILED DESCRIPTION OF THE INVENTION

The present invention provides a cascade polymer coated molecule and a method of forming the same. The method generally includes the steps of dendrimerizing a mixture of branched monomers on a substrate wherein the monomers have heterogenously functionalized branches and homogenous connectivity to the substrate.

The term "substrate" is defined more particularly in the background art section of the present application and is used generally herein. The substrate can be a core molecule, such as found in classic, small, carbon-based molecules possessing nucleophiles such as nitrogen, or an extended cascade polymer having a surface area which is then dendrimerized in accordance with the present inventive method. Such cascade polymers, in the forms of unimolecular micelles, are disclosed in detail in the U.S. Pat. Nos. 5,154,853 and 5,206,410, both to applicants of the present invention. Examples of such substrates are silica based substances, functionalized classical linear polymers, functionalized classical micelles, microgels, spherical polymers, as well as multifunctionalized or monofunctionalized inorganic and organic molecules. Examples of such molecules are polysiloxanes, polysaccharides, and the like. Most generally, the present invention can be employed to "dendrimerize" any common material(s) possessing an acidic proton(s).

The term "dendrimerizing" or "dendrimerize" relates to the application, in a tier or layering type manner, of monomers which chemically bond to reactive surface groups. As stated above, the common denominator that related the reactive surface groups on the substrate surface is that the reactive groups include an acidic proton. Thus, the dendrimerizing step characterizing the present invention involves the tiering or layering of at least one monomer layer, or several monomer layers, over a reactive surface. Since functional groups including acidic protons can be found on most common materials, the present invention has broad application as a means of coating or forming a surface layer on a wide variety of substrates. Since the monomer utilized with the present invention can have a wide range of functionalities, as described in the copending U.S. patent application Ser. No. 08/626,395 as previously cited, the present invention can have a wide range of utilities by imparting a wide range of desired properties to a surface of a wide range of substrates. In other words, the scope of utility of the present invention is enormous.

As stated above, the inventive method is characterized by the step of dendrimerizing a mixture of branched monomers on a substrate. Preferably the branched monomers are stable multifunctionalized, and preferably trifunctionalized, isocyanates. Such isocyanates are described in detail in the copending patent application Ser. No. 08/626,395, cited above. Chemically, such isocyanates can be characterized by the formula $$O=C=N-C(CH_2-R)_3$$

with R being selected from the group including:
a) $-CH_2-CH_2-COOR'$
b) $-O-CH_2-CH_2-COOR$;
c) $-O-CH_2-CH_2-CN$, or
d) $-CH_2-CH_2-O-R''$
with R' being selected from the group consisting of alkyl, cycloalkyl, aryl, heteroaryl, polycycloalkyl, adamantyl;
with R'' being selected from the group consisting of alkyl, cycloalkyl, aryl and heteroaryl ester functionality, and sulfur or a silicon bearing substituents selected from the group including:

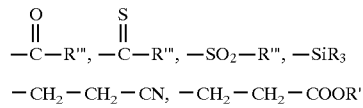

wherein R''' is alkyl (C-1 to C-20) cycloalkyl (C3-C-10), aryl, aralalkyl heteroaryl, polycycloalkyl, and adamantyl.

This formula is only exemplary of the isocyanates and is not intended limit the broad scope of multifunctionalize isocyanates capable of use in accordance with the present invention.

In utilizing the combinatorial chemistry approach, the present invention is characterized by the step of dendrimerizing the mixture of branched monomers on the substrate wherein the monomers have heterogeneous functionalized branches and homogenous connectivity to the substrate. The monomers which are dendrimerized to the surface layer of the substrate are not a homogenous batch having a single functionality but rather a mixture of different monomers having different functionalized branches. Some of the monomers may have carboxyl termini, some of the branches may have alcohol termini, some of the branches may have ester termini, etc. Hence, the resulting coated substrate possesses a cascade polymer coating consisting essentially of the substrate surface having at least one dendrimerized surface layer consisting of heterogeneous functionalities, the layer being linked to the substrate by a series of homogenous linkages. By using the preferred isocyanate building blocks, the homogenous linkages are of the formula

Thus, the application of the present invention utilizes the combinatorial method of dendritic construction by using mixtures possessing various compositions of different isocyanate based monomers for sequential tier formation. The present invention can be utilized to form a single surface layer or multiple tiers in a cascade polymer type expansion. The present invention can be termed "combinatorial expansion chemistry" as the combinatorial chemistry is utilized in an ever expanding layering or tier formation. With further tier formation, the functionalization of the surface densifies because of the multiplicity of the dendrimeric process.

In the process of the present invention, identical mixtures consisting of the same monomer composition can be used at each tier or the composition can be varied. Also, combinatorial tier growth can be employed in concert with standard tier construction whereby a unit compositional tier is added.

The combinatorial chemistry approach thereby provides a mixture of surface functionalities. This mixture of surface functionalities is reflective of the ratio of the mixture of branched monomers utilized in the dendrimerizing step of the present invention. That is, during the dendrimerizing step, the substrate is reacted with the mixture of monomers having a predetermined ratio of component functionalities. The dendrimerized surface is formed and includes a layer of monomers consisting of a mixture of functionalities of the same predetermined ratio as that of the mixture of monomers having been reacted. Hence, the nature of the functionalities on any given surface can be predetermined by the formation of the mixture of monomers used to form that layer.

More specifically, the dendrimerizing step can be further defined as reacting the monomer mixture with the substrate surface wherein the monomer mixture consists of compounds of the formula OCN- wherein—is a mixture of protected functionalities, at least some of the protected functionalities possessing complimentary protective groups

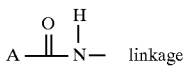
linkage is formed between the substrate surface and each of the monomers. The complimentary protected groups are then deprotected resulting in a heterogeneous surface layer reflecting the heterogeneous mixture of the deprotected functionalities. Accordingly, the combinatorial tier construction of the present invention employs complimentary protection and deprotection strategies at the same stage of molecular growth. This is in contrast to prior art methods which result from traditional protection-deprotection generational manipulation. The present invention derives from tier construction using a mixture (of any desired composition) of functionally compatible monomers in similar monomer connectivity, preferably isocyanate based.

With regard to the terms used above, the term "protected functionalities" is used in its common chemical sense. That is, during the iterative process, the functionalities which terminate the branches of the monomer must be protected during the iterative process to prevent their untimely reactivity. When further branching or tiering is desired or if exposure of the functionalities is desired, the branches are then deprotected by means well known in the art so as to expose the functionalities. One permutation of the present invention utilizes functionalities on different monomers which are all complementary such that all of the protected groups can be deprotected. An alternative embodiment, exemplified below, is where some of the functionalities are not complementary and thereby not deprotected. As used herein, complimentary is used in its known connotation, referring to protection or protective groups "logically" chosen on different monomers in the same reaction. When deprotection of one or more is desired, the logically chosen other protective groups will not interfere or be affected. In this manner, further tier formation will extend from the deprotected branches but not from the protected branches. Thus, internal functionalities can be created on shorter branched arms which were protected and remain protected during the iterative process but can be deprotected, if desired, at a later step.

FIG. 1 illustrates one permutation or embodiment of the combinatorial process of the present invention. "Diversified" surface functionalization and tier construction using a generic dodecaamine dendrimer(1) is affected by treatment with a "stoichiometrically correct" mixture of three different isocyanate monomers possessing complementary protective groups. In this example, the mixture consists of 33% trisnitrile

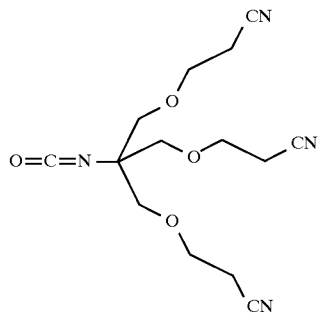

42% of a triacetate

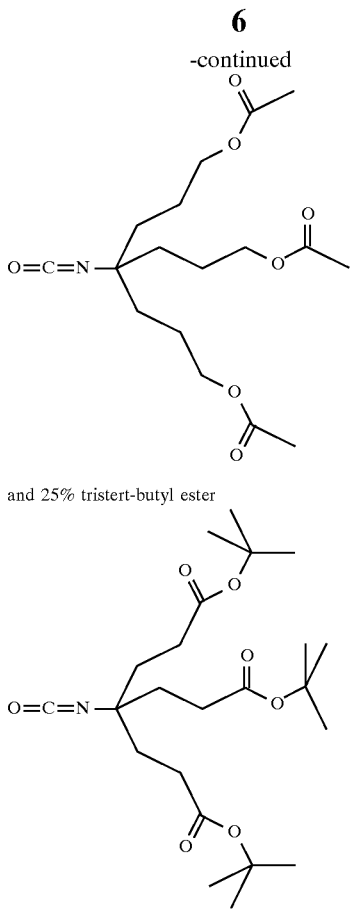

and 25% tristert-butyl ester

This reaction results in dendrimers, as exemplified by compound 2 in FIG. 1, possessing a new generation or layer with a surface composition similar to the monomer mixture composition. Subjection of the multifunctional dendrimers derived thereby to basic transesterification[5] utilizing potassium carbonate and ethanol, and reduction utilizing Raney nickel[6] or cobalt[3] will sequentially deprotect the alcohol and amine termini leaving the masked carboxylic acids intact to afford the poly(aminoalcohol), compound 3, in FIG. 1. Repetition of this combinatorial procedure, using different composition mixtures of isocyanate monomers, yields second generation multicomponent dendrimers such as dendrimer 4 in FIG. 1.

The combinatorial procedure is well suited to superstructure property and architectural modification of dendrimers and appropriately functionalized materials. Thus, distinctive void regions or cavities can be crafted into the branched framework that can be employed for such processes as guest molecule hydrolysis reactions provided that appropriate hydrolytic functionality has been incorporated at or near the cavity. Rapid construction and screening of materials with varying compositions follow protocols very similar to that currently employed for small molecule library (usually pharmaceutical)screening[7], although hydrolytic processes are exploited such as shown as dendrimer 5 in FIG. 2.

In view of the above, a cascade polymer coated molecule can be constructed consisting essentially of a substrate including a surface and at least one dendrimerized surface layer consisting of heterogeneous functionalities, the surface layer being linked to the substrate by homogenous linkages. Preferably, at least some of the functionalities are deprotected and linked to the substrate by linkage of the formula

The substrate surface can include functional groups selected from the group derived from stable trifunctionalized isocyanates. The groups can consist of aryl, alkyl and arylalkyl alcohols, carboxyls, esters, and other reactive groups possessing an acidic proton.

The present invention possesses utility in various area of surface coating and polymer production. For example, the present inventive synthesis can be used to derive protective coatings, such as hydrophilic coatings for fabrics such as filters, hospital gowns, operative curtains, and the like. By controlling the functionalized termini of the monomers, various levels of hydrophobicity can be obtained on a functionalized surface made in accordance with the present invention. Hence, wetting of surfaces can be controlled so as to form super wet or super dry materials. Likewise, protective coatings can be formed having heterogeneous functionalities thereon. As disclosed in copending patent application Ser. No. 08/280,591, heterogeneous functionalities can be incorporated into or onto surfaces having various catalytic sites therein. Thereby, a series of reactions can be accomplished on the surface of a molecule.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically describe.

REFERENCES

1. Newkome, G. R., Weis, C. D., Pats. Appld. for 1996.
2. Newkome, G. R., Weis, C. D., *Org. Prep. Proc. Int.*, 1996, to be submitted.
3. Worner, C., Mulhaupt., R. *Agnes Chem., Int. Ed. Engl.* 1993, 32, 1306; *Agnew. Chem.* 1993, 105, 1367; deBrabander-van den Berg, E. M. M., Meijer, E. W. *Agnew Chem., Int. Ed. Engl.* 1993, 32, 1308; *Agnew. Chem.* 1993, 105, 1370.
4. Xiang, X.-D., Sun, X., Briceño, G., Lou, Y., Wang, K.-A., Chang, H., Wallace-Freedman, W. G., Chen, S.-W., Schultz, P. G. *Science* 1995, 268,1738.
5. Plattner, J. J., Wless, R. D., Rapoport H., *J. Am. Chem. Soc.* 1972, 94, 8613.
6. van Gendersen, M. H. P., Baars, M. W. P. L., van Hest, J. C. M., de Brabander-van den Berg, E. M. M., Meijer, E. W., *Recl. Trav. Chim. Pays-Bas.* 1994, 113,573; Domingeuz, X. A., Lopez, I. C., Franco, R. *J. Org. Chem.* 1961, 26, 1625.
7. Carell, T., Wintner, E. A., Sutherland, A. J., Rebek, J., Jr., Dunayevskiy, Y. M., Vouros, P., *Chem. Biol.* 1995, 2, 171, Carell, T., Wintner, E.

A., Bashir-Hashimi, A., Rebek, J., Jr. *Agnew Chem., Int. Ed. Engl.* 1994, 33, 2059.

What is claimed is:

1. A method of forming a branched surface layer on a substrate by dendrimerizing with a mixture of branched monomers on the substrate and producing heterogeneously functionalized substrate branches and homogenous monomer connectivity.

2. A method of forming a branched surface layer on a substrate by dendrimerizing with a mixture of branched monomers on the substrate and producing heterogeneously functionalized substrate branches and homogenous monomer connectivity, dendrimerizing step is further defined as dendrimerizing the mixture of branched monomers on the substrate by an isocyanate reaction.

3. A method as set forth in claim 2 wherein said dendrimerizing step is further defined as reacting the monomer mixture with the substrate surface wherein the monomer mixture consists of compounds of the formula O=C=N (CH$_2$—R)$_3$ with R being selected from the group including:

a) —CH$_2$—CH$_2$—COOR',
   b) —O—CH$_2$—CH$_2$—COOR',
   c) —O—CH$_2$—CH$_2$—CN, or
   d) O—CH$_2$—CH$_2$—X—R"

wherein R' is selected from the group consisting of alkyl, aryl, heteroaryl, and aralakyl; X is selected from the group consisting of O, N, S, and P; and
   wherein R" is selected from the group consisting of alkyl, cycloalkyl, aryl and heteroaryl ester functionality.

4. A method as set forth in claim 3 including protected functionalities possessing complementary protective groups, said method including the step of deprotecting all of the functionalized groups of the layer of monomers.

5. A method as set forth in claim 4 wherein at least one of the monomers in the mixture of monomers is not deprotected during said deprotecting step.

6. A method as set forth in claim 5 further including the step of dendrimerizing a second layer of monomers over the first layer of the monomer mixture, the monomers not deprotected remaining unreactive resulting in a second layer reacted and linked with only the deprotected functionalities of the first dendrimerized layer.

7. A method of forming a branched surface layer on a substrate by dendrimerizing with a mixture of branched monomers on the substrate and producing heterogeneously functionalized substrate branches and homogenous monomer connectivity, wherein said branched monomers are stable trifunctionalized isocyanates.

8. A method as set forth in claim 1 wherein said dendrimerizing step is further defined as reacting the substrate with a mixture of the monomers having a predetermined ratio of components functionality and forming the dendrimerized surface including a layer of the monomers consisting of a mixture of functionalities of the same predetermined ratio.

9. A cascade polymer coated molecule consisting essentially of a substrate including a surface and at least one dendrimerized surface layer consisting of heterogeneous functionalities and linked to said substrate by homogeneous linkages, wherein said functionalities are not protected and are linked to said substrate by a linkage of the formula:

10. A molecule as set forth in claim 9 wherein functionalities are deprotected and linked to said substrate by a linkage of the formula.

* * * * *

UNITED STATES PATENT AND TRADEMARK OFFICE
CERTIFICATE OF CORRECTION

PATENT NO. : 5,886,126
DATED : March 23, 1999
INVENTOR(S) : Newkome et al.

It is certified that error appears in the above-identified patent and that said Letters Patent is hereby corrected as shown below:

Column 2, line 51, delete "FIG. 1" and insert --FIG. 1A--

Column 2, line 51, after "schematic" insert --symbolic--

Column 2, line 53, delete "and" and insert --FIG. 1B defines the symbols of FIG 1A; and--

Column 5, line 45, delete "FIG. 1" and insert --FIGS 1A and 1B--

Column 6, line 36, delete "FIG. 1" and insert --FIG. 1A--

Column 6, line 44-45, delete "FIG. 1" and insert --FIG. 1A--

Column 6, line 48, delete "FIG. 1" and insert --FIG. 1A--

Signed and Sealed this

Twenty-seventh Day of July, 1999

Attest:

Q. TODD DICKINSON

*Attesting Officer*  *Acting Commissioner of Patents and Trademarks*